United States Patent [19]

Kingsley

[11] Patent Number: 4,634,680

[45] Date of Patent: Jan. 6, 1987

[54] SEQUENTIAL ELUTION PROCESS

[75] Inventor: Ilse S. Kingsley, Bethlehem, Pa.

[73] Assignee: International Coal Refining Company, Allentown, Pa.

[21] Appl. No.: 513,543

[22] Filed: Jul. 14, 1983

[51] Int. Cl.$^4$ .................. G01N 33/24; B01D 11/02
[52] U.S. Cl. ............................. 436/178; 436/161;
422/70; 210/634; 210/786
[58] Field of Search .............. 436/178, 161; 422/70;
210/634, 786; 73/61.1 C

[56] References Cited

U.S. PATENT DOCUMENTS 3,249,403 5/1966 Boehinski et al. ............... 422/89
4,279,755 7/1981 Himsley ........................ 210/688

FOREIGN PATENT DOCUMENTS 1148662 4/1969 United Kingdom .

OTHER PUBLICATIONS

Bodusynski et al., "Separation of Solvent-Refined Coal Into Solvent Derived Fractions" *Analytical Chemistry*, vol. 54, No. 3, pp. 372-375 (3/82).
Bodusynski et al., "Separation of Solvent-Refined Coal Into Compound Class Fractions" *Analytical Chemistry*, vol. 54, No. 3, Mar. 1982.
Awadalla et al., "Alternative Procedure for the Analysis of Coal-Derived Materials for Oil, Asphaltene and Pre-Asphaltene Content" *Fuel* vol. 61, Nov. 1982, pp. 1168-1170.
Schweighard et al., "Solvent Extraction of Coal-Derived Products", *Analytical Chemistry*, vol. 50, No. 9, Aug. 1978, pp. 1381-1382.
Burke et al., "Liquid Column Fractionation; A Method of Solvent Fractionation of Coal Liquefaction and Petroleum Products" *Fuel*, vol. 58, Jul. 1979, pp. 539-541.
Farcasiu, "Fractionation and Structural Characterization of Coal Liquids" *Fuel* vol. 56, Jan. 1977, pp. 9-14.
Meier zu Koecker, "Continuous Fluidized-Bed Extraction and Catalytic Extract Hydrogenation" CA99(22):178741z (1983).
Meier zu Koecker, "Study of Extracts Obtained by Fluidized-Bed Extraction" CA97(26):219320r (1982).

*Primary Examiner*—Barry S. Richman
*Assistant Examiner*—Michael S. Gzybowski

[57] ABSTRACT

A process and apparatus for the separation of complex mixtures of carbonaceous material by sequential elution with successively stronger solvents. In the process, a column containing glass beads is maintained in a fluidized state by a rapidly flowing stream of a weak solvent, and the sample is injected into this flowing stream such that a portion of the sample is dissolved therein and the remainder of the sample is precipitated therein and collected as a uniform deposit on the glass beads. Successively stronger solvents are then passed through the column to sequentially elute less soluble materials.

12 Claims, 1 Drawing Figure

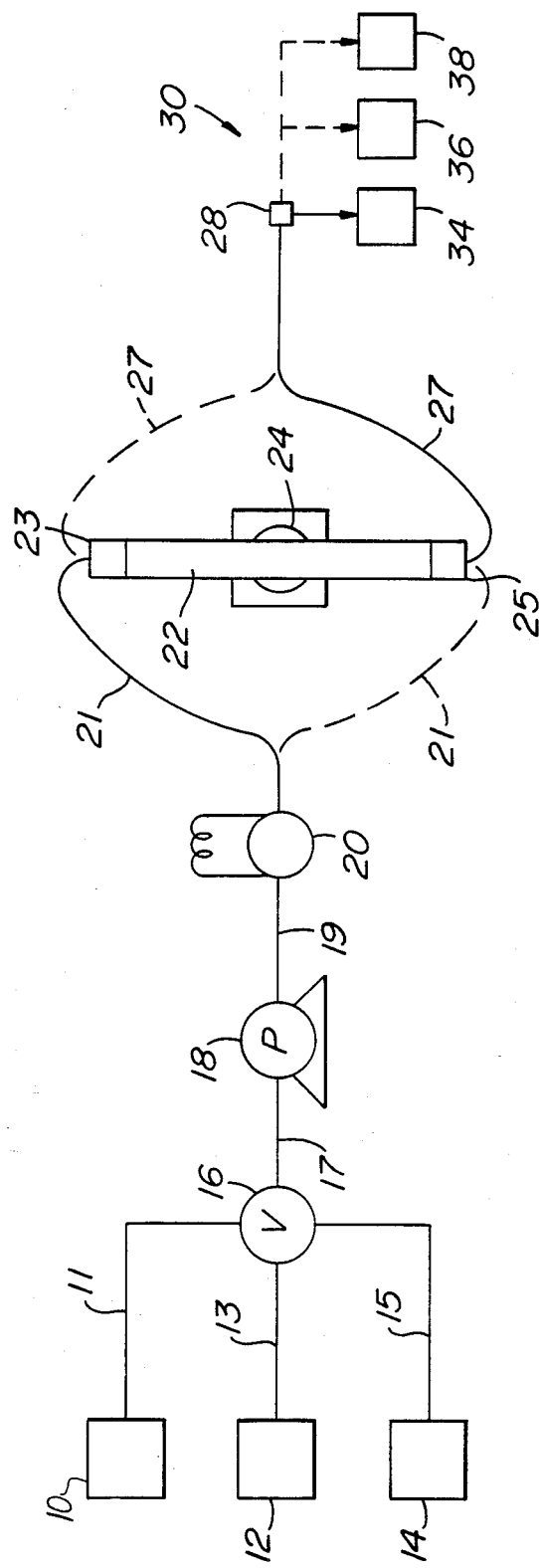

SEQUENTIAL ELUTION PROCESS

The Government of the United States of America has rights in this invention pursuant to Contract No. DE-AC05-78OR03054 (as modified) awarded by the U.S. Department of Energy.

BACKGROUND OF THE INVENTION

This invention relates generally to a process and apparatus for the separation of complex mixtures of carbonaceous materials by sequential elution with solvents. More particularly, the invention relates to a process and apparatus for the separation of molecular constituents of coal-derived material such as coal liquefaction process streams.

In processes such as the SRC-I process for the solvent refining of coal by thermal liquefaction there is a need for the separation and characterization of coal-derived oils. While many procedures have been used over the past forty years to monitor coal conversion products, no standard procedure has evolved that is widely used to separate and characterize liquefied or solvent refined coal products. The problems with the prior procedures are that they give low or high material balance, are time consuming, and/or involve frequent subjective judgments.

The state of the prior art is described in the following prior art materials:

(1) ANALYTICAL CHEMISTRY, Volume 50, No. 9, August, 1978, page 1381+, Article Entitled "Solvent Extraction of Coal-Derived Products", (2) FUEL, Volume 58, July, 1979, pages 539–541, Article by Burke et al. Entitled "Liquid Column Fractionation; A Method of Solvent Fractionation of Coal Liquefaction and Petroleum Products."

(3) Advanced Technology Section of the Chemical Technology Division, Oak Ridge National Laboratory, Summer, 1981, Article by Denton et al. Entitled "Development of an Automated Coal Fractionation System."

(4) FUEL, Volume 56, January, 1977 pages 9–14, Article by M. Farcasiu. Entitled "Fractionation and Structural Characterization of Coal Liquids."

(5) ANALYTICAL CHEMISTRY, Volume 54, No. 3, March, 1982, pages 372–381, Articles by Boduszynski et al. Entitled "Separation of Solvent-Refined Coal Into Solvent-Derived Fractions" and "Separation of Solvent-Refined Coal Into Compound-Class Fractions."

(6) U.S. Pat. No. 4,279,755 for "Continuous Countercurrent Ion Exchange Process."

(7) FUEL, Volume 61, November, 1982, pages 1168–1170, Article by Awadalla et al. Entitled "Alternative Procedure for the Analysis of Coal-Derived Materials for Oil, Asphaltene and Pre-asphaltene Content."

The above references are illustrative of the known art for separating very complex mixtures of carbonaceous materials using a sequence of successively stronger solvents to obtain oils, asphaltenes and preasphaltenes fractions. These different prior art techniques for carrying out this sequential extraction range from the use of sonification and centrifugation, as described in Reference (1), to using a column packed with glass beads, as in References (2) and (5), or a column packed with sand in combination with active silica packing, as in Reference (3), or a column packed with silica gel, as in Reference (4). All of the prior art techniques either employ packed columns or involve a batch type of process. While Reference (6) uses a fluidized bed, it relates to the use of a column of material used as an ion exchange resin, which material interacts with the sample and would not be applicable to the process of the invention. Reference (7) is a batch type of process in which the entire sample is coated on the bed prior to the sequential solvent extraction procedure.

Various of the above-described analytical workup procedures have been used to determine the amount of distillate, oils, asphaltenes, preasphaltenes and residue in SRC-I process streams. However, these procedures are time-consuming and are not always reliable in terms of the material balances of the fraction generated around specific units, such as, for example, the Kerr-McGee Critical Solvent Deashing Unit. Hence, there is a need to minimize turnaround time and maximize reliability in these analytical workup procedures.

It has been shown that commonly used distillation procedures yield different amounts of distillate from the same sample and that, due to thermal degradation, distillation may alter the product distribution of preasphaltenes and residue. Laboratory vacuum distillation must therefore be carried out under well-defined conditions, and should only be used to generate a distillate and not a distillate bottoms for subsequent analysis, such as the determination of asphaltenes, preasphaltenes, and residue.

Various extraction techniques will generate different amounts of oils, asphaltenes, preasphaltenes, and residue. These techniques include beaker extractions, Soxhlet extraction, beaker precipitations, solvent separation/filtration and Liquid Column Fractionation (LC/F), developed by Conoco. Most of these procedures are very time-consuming and demand great operational skill.

The turnaround time (the time elapsed from the beginning of the analysis until the time when a result is generated including both the hands-on analysis time and the unattended analysis time) for these procedures is a very important factor in process monitoring and in cost. For example, the fastest appears to be the LC/F procedure which may provide a turnaround time of the order of about nine hours for an unknown sample type. The Soxhlet and beaker extractions in combination with the beaker precipitation method for the oils/asphaltenes separation may require about five manhours of analysis time; however, the turn-around time is of the order of about two days. The sequential solvent extraction method may take about twelve manhours and the turnaround time is also about two days.

In addition to analysis time, another criterion for a reliable product workup procedure is the material balance of the weight percents from the fractions generated. If two different samples are analyzed for fraction composition, and an equal mixture (by weight) of the samples is prepared and analyzed to determine its fraction composition, the fractions obtained should match the arithmetic average of the fractions from the two initial samples. It has been shown that beaker extractions, Soxhlet extractions, beaker precipitation, and sequential solvent extraction do not generate all fractions in the same additive manner, i.e., closing the material balance.

SUMMARY OF THE INVENTION

It is the general object of the invention to provide a process and apparatus for the separation of complex mixtures of carbonaceous material by sequential elution with solvents wherein the separation is achieved in an accurate and time efficient manner. The process and apparatus of the invention has reproducibility of results, a minimum analysis time and results in an accurate material balance of the fraction.

The invention differs from the known art by employing a unique procedure whereby a fractionation column consisting of glass beads is maintained in a fluidized bed with high volume solvent flow while the sample is added. The advantage of this procedure is that materials can be analyzed with a high degree of reproducibility (plus or minus 1% by weight) and the fraction shows complete additivity for oils, asphaltenes and preasphaltenes.

The method and apparatus of the invention requires analysis time of about one hour per sample which is a signficant improvement over any SRC-I characterization method presently available. As compared with the liquid column fractionation method, which has the fastest turnaround time, the method and apparatus of the invention eliminates the distillation step required in the liquid column fractionation method and, therefore, quantifies the oils fraction directly in one extraction step.

Briefly stated, a novel feature of the process and apparatus of the invention is the use of an extractor section comprised of a tubular column filled with glass beads or other low surface, inert material. A sample, which is to be separated, is dissolved in a strong solvent, and the column containing the glass beads is maintained in a fluidized state by a rapidly upward flowing stream of the first (weakest) extracting solvent, the sample being injected into this flowing stream such that the small portion of strong solvent is immediately diluted in the weak flowing solvent to thereby precipitate all materials which are insoluble in this weak solvent. The precipitated material is then collected as a uniform deposit on the glass beads. In accordance with the process and apparatus of the invention at least one other stronger solvent, and up to several additional successively stronger solvents, are passed through the column to sequentially elute successively more difficult soluble materials. The sample material deposited on the beads is ultimately removed by using a sufficiently strong solvent.

In the case of analyzing an SRC-I process stream to determine the amount of oils, asphaltenes and preasphaltenes, the use of the fluidized bed in the process of the invention is such that the oils are dissolved in a large volume of the first (weakest) extracting solvent used whereby the co-solubility effect of the oils is eliminated. In prior methods using a packed bed, the oils are concentrated in a small volume and solubilize some of the asphaltenes and preasphaltenes. This causes an imprecise determination of the amount of the fractions.

BRIEF DESCRIPTION OF THE DRAWING

The single FIGURE is a schematic view of the apparatus used for performing the process in accordance with the invention.

DETAILED DESCRIPTION OF THE PREFERRED EMBODIMENT AND BEST MODE

While the preferred embodiment of the invention shown in the drawing and to be described hereafter is particularly adapted for the solvent extraction of heptane soluble, benzene soluble and pyridine soluble constituents of a coal-derived material, it will be apparent that the invention is more broadly applicable to analytical procedures for the handling of various types of samples. For example, the invention is applicable to various natural product extraction procedures such as shale, tar sand and petroleum products, and to various pharmaceutical and biochemical applications.

Moreover, the process and apparatus can be utilized in analogous analytical procedures involving multiple solvent extractions of a multitude of materials, utilizing a broad spectrum of solvents having different solvent properties, but employing the novel features of the invention. For the purpose of the present invention, it is understood that solvent properties include, but are not limited to, polarity, ionic strength, dipole moment, pH, density and viscosity.

In accordance with preferred embodiment, the apparatus of the invention is shown in the Drawing and comprises means providing a supply of three solvents arranged in order of increasing polarity, such means comprising three liquid reservoirs 10, 12 and 14 containing supplies of the solvents heptane, benzene and pyridine, respectively. The reservoirs 10, 12 and 14 are connected by conduits 11, 13 and 15, respectively, to the inlet ports of a rotary 4-way switching valve 16. The outlet port of switching valve 16 is connected by a conduit 17 to a solvent metering pump 18. Pump 18 is of a type capable of pumping precisely, i.e., plus or minus 0.01 ml/min, at a flow rate of 10 ml/min. The discharge of pump 18 is connected via a conduit 19 to an injection loop 20 which comprises a sample injection valve having a loop size of 0.5 ml. The injection loop 20 may be of any type well known in the art capable of injecting a predetermined amount of a sample into the solvent stream flowing from the pump 18.

A conduit 21 delivers the solvent stream containing the sample from the outlet of injection loop 20 to the inlet of a glass column 22. Column 22 is 9×250 mm in size and is provided with an inlet end fitting 23 and an outlet end fitting 25 for attachment to conduits 21 and 27, respectively, conduit 27 providing for flow from the outlet end of column 22. There is provided a mounting means 24 for column 22, such mounting means being capable of supporting the column 22 in a vertically extending position and for turning column 22 through 180 degrees rotation to reverse the orientation of the inlet and outlet ends thereof for a purpose to be described more fully hereafter.

The discharge end of conduit 27 is connected to a movable support 28 of a fraction collector 30. Support 28 is movable horizontally for positioning the discharge end of conduit 27 over three 120 ml glass collection vials 34, 36 and 38.

The manner of assembly of the above-described apparatus will be apparent. End fittings 23 and 25 and other conduit connections are adapted for connection with the associated conduits 11-27, which preferably are Teflon tubing having a diameter of one-eighth inch and a wall thickenss of one-thirty second of an inch.

Other apparatus not shown on the Drawing for performing the analytical procedures of the invention includes a dry bath having a controllable temperature at 80° C. plus or minus 1° C. and 30° C. plus or minus 1° C., a supply of nitrogen at 9 psig, and an analytical balance capable of weighing 120 g, plus or minus 0.1 mg.

In preparation for the performing a preferred embodiment of the process of the invention, reservoir 10 is partially filled with n-heptane (HPLC grade), reservoir 12 is partially filled with benzene (pesticide grade), and reservoir 14 is partially filled with pyridine (analytical grade). When a new column 22 is to be used, its content must be washed and conditioned. To this end, column 22 is filled with 13.4 g of 90–120 mesh glass beads which are contained in column 22 by filter discs at each end. Conduit 21 is connected between inlet end fitting 23 and the outlet of the injection loop 20, and conduit 27 between outlet end fitting 25 and movable support 28 of fraction collector 30. Column 22 is mounted vertically on the mounting means 24 with its inlet end on the bottom and its outlet end on the top, conduits 21 and 27 taking the dashed position shown in the Drawing. The glass beads are then washed at a flow rate of 10 ml/min for about ten minutes with n-heptane, then for ten minutes with benzene, and finally for ten minutes with pyridine. This is followed by fifteen minutes of washing with heptane. The flow through column 22 is then stopped whereby the glass beads have been washed and conditioned and column 22 is ready for sample injection. A column prepared in this manner can usually be used for 100–200 samples before changing is necessary.

The glass beads provide a low surface, inert material, "low surface" referring to a smooth surface as opposed to a porous surface.

The sample fractionation by the process in accordance with this preferred embodiment of the invention is performed in sequential steps as follows:

(1) Weigh collection vials 34, 36 and 38 for each sample on an analytical balance and record weight within 0.1 mg.

(2) Fill injection loop vials with 20% solution of sample in tetrahydrofuran (THF) and load into injection loop 20.

(3) Set valve 16 and pump 18 to provide heptane flow at 10 ml/min upward flow through column 22 fluidizing the bed of glass beads. A fluidized bed is achieved when all the glass beads are suspended in column 22 without resting at any point on one another. This is the commonly understood description of a fluidized bed.

(4) At time zero, actuate injection loop 20 to inject the sample into the solvent stream flowing through column 22 and start collecting effluent in first collection vial 34.

(5) At time 1.5 minutes, turn column 22 180° clockwise thereby causing downward flow and switching from a fluidized bed to a packed bed.

(6) At time 9.0 minutes, switch valve 16 to provide flow of benzene at 10 ml/min rate.

(7) At time 9.2 minutes, switch effluent to second collection vial 36. First vial 34 contains the oils fraction.

(8) At time 17.0 minutes, turn column 22 180° counter-clockwise causing upward flow therethrough.

(9) At time 18.0 minutes, switch valve 16 to provide flow of pyridine at 10 ml/min rate.

(10) At time 18.2 minutes, switch effluent to third collection vial 38. Second collection vial 36 contains asphaltenes fraction.

(11) At time 21.5 minutes, turn column 22 180° clockwise causing downward flow therethrough.

(12) At 23.5 minutes, switch valve 16 to provide flow of heptane at 10 ml/min rate.

(13) At time 27.2 minutes, switch effluent from third vial 38 to waste. Third vial 38 contains preasphaltenes fraction.

(14) At time 31 minutes, turn column 22 180° counter-clockwise causing upward flow. Stop flow to allow glass beads to settle. Column 22 is now reconditioned with heptane and ready for injection of new sample.

The above-described time sequence was determined to provide very high reproducibility for various types of samples.

The solvent removal procedure is then carried out in a well ventilated hood as follows:

(1) After the three fractions are collected as described above, place vials 34, 36 and 38 in a constant temperature dry bath at 80° C. and remove solvents by blowing nitrogen over the surface of the sample not exceeding 9 psig. Avoid any splashing.

(2) Solvent has been removed if the vial content looks dry (or oily for the oils fraction).

(3) Place vials 34, 36 and 39 into a dry bath at 30° C. for 30 minutes, blowing a stream of nitrogen into the vials. Then cap and weigh each vial. Repeat this step as many times as necessary to reach a constant weight. The weight obtained should be within 0.1 mg precision.

The calculation steps to determine the weight of each of the fractions are as follows:

(1) Determine the weight of each fraction by subtraction of the weight of the empty collection vial from the weight of the sample-containing-vial. Add the weight of all three fractions to determine the total weight recovered.

(2) Normalize the weights to weight percent (wt%):

$$\text{wt \% oils} = \frac{\text{mg oils}}{\text{total mg recovered}}$$

$$\text{wt \% asphaltenes} = \frac{\text{mg asphaltenes}}{\text{total mg recovered}}$$

$$\text{wt \% preasphaltenes} = \frac{\text{mg preasphaltenes}}{\text{total mg recovered}}$$

(3) Normalize the weight percents to total fractional distribution, if THF insoluble residue was present in the original sample:

(a) Determine weight of residue (obtained in procedure for preparation of THF pyridine solubles prior to analysis in accordance with the invention.

(b) Calculate the factor $$\frac{(100 - \text{wt \% residue})}{100}$$

(c) Multiply each wt% obtained in step (2) with this factor to obtain a total fractional distribution.

It will be evident that in the procedure described in detail above the use of a fluidized bed of glass beads in a column allows the injected THF-soluble sample fraction to be rapidly dispersed in n-heptane, thereby precipitating heptane-insoluble material (asphaltenes and preasphaltenes) on the glass beads in a uniform manner. The solvent-metering pump 18 delivers heptane through the column, eluting the oils fraction from the sample. It is noted that most of the oils are dissolved and collected in the 1.5 minute period of step (4) of the sample fractionation process when a fluidized bed is maintained and only a small amount of oil is dissolved and collected in step (5) when a packed bed is maintained. Pumping of heptane at a 10 ml/min flow rate through the column is followed by pumping each of benzene and pyridine, thereby eluting the asphaltene and preasphaltene fractions, respectively. The inverting of column 22 at step (8) to return to upward flow during elution with pyridine serves to compensate for the difference in specific gravity between pyridine and benzene, thereby to achieve faster elution and eliminate backmixing. The initial inverting of column 22 (step 5) improves the distribution of the glass beads and prevents the formation of channels for the solvent to flow through bypassing contact with the glass beads. After the three fractions are collected, the solvent is evaporated in a dry bath at 80° C. under a nitrogen stream, and then weighed to obtain the weight percent distribution of oils, asphaltenes and preasphaltenes in the THF-soluble portion of the sample. The column is regenerated with heptane before the next sample is analyzed.

It will be apparent that various changes may be made in the apparatus and method of the invention within the scope thereof as defined by the following Claims. For example, the valve of injection loop 20 can be either manually or automatically operated and injection loop 20 may comprise a sample loop varying in size. Also, the size of the column 22 can be decreased by 80% in volume if the sample size is decreased and can be increased to full preparative scale if desired. Further, column 22 can be made of any inert material such as 316 stainless steel etc. and the mounting for column 22 can be such that it can be rotated by manual or automatic means. Also, the fraction collector 30 can be of either a manual or automated means if desired. Any number of solvents may be used depending on the sample composition complexity, it being noted that for coal liquefaction process streams use of solvents of increasing polarity is important. For example, heptane can be replaced by any alkane, (provided that the boiling point of such solvent is significantly lower, about 75° C. or more, than the lowest boiling compound in the sample fraction) benzene can be replaced by toluene, and pyridine can be replaced by THF. Also, the Teflon tubing can be replaced by any suitable inert material capable of withstanding the head pressures of 300 psi, such as for example, glass or stainless steel. Further, the dry bath temperature range will be dependent upon the boiling points of the extracted solvent and the extracted components, the boiling point of the solvent being significantly lower than that of the extracted components to allow complete solvent removal without sample loss. Further, the nitrogen pressure may be varied so as to allow evaporation of the solvent over a short period of time.

EXAMPLE

A solvent refined coal (SRC) sample from the Wilsonville, Alabama SRC-I pilot plant (Run No. 220 B-MB) was dissolved in tetrahydrofuran (THF) to make a 20 percent solution. 0.5 ml of the 20% solution was then injected into a glass column (9×250 mm) which contained 13 g glass beads (100 mesh) and which were fluidized by upward flow of 10 ml/min heptane. Continuing the heptane flow, the sample was rapidly mixed in the fluidized bed of glass beads, depositing heptane insoluble material on the glass beads, diluting the solvent THF by a factor of 1:40 and extracting the heptane soluble fraction—oils—from the sample. The oils fraction was extracted for 9 minutes and collected in a pre-weighed glass vial. Then the extracting solvent was switched to a stronger solvent—benzene—which was pumped through the column at 10 ml/min extracting the benzene soluble fraction—asphaltenes—from the sample. The asphaltenes fraction was extracted for 9 minutes and was collected in a second pre-weighed glass vial. Then the extracting solvent was switched to an even stronger solvent—pyridine—which was pumped through the column at 10 ml/min solubilizing the remaining fraction—preasphaltenes, which was collected in a third pre-weighed glass vial. Finally the extracting solvents were evaporated from the three vials at 80° C. under a steady stream of nitrogen and brought to constant weight at 30° C. under nitrogen. The weights obtained represented the weight distribution of the three fractions—oils, asphaltenes and preasphaltenes—in the SRC sample.

An evaluation of the analysis results of the process in accordance of the invention (hereinafter designated by "ASE") was made as follows:

Approach

Six different SRC-I process streams were analyzed by the ASE procedure, and the results were evaluated for reproducibility and material balance (MB) of the fractions. The samples were generated at the Wilsonville Advanced Coal Liquefaction Facility during Run No. 220 (B-MB).

To evaluate the material balance of the analyzed fractions, two mixtures of the samples were prepared; the first was a 50/50 volume percent (vol %) mixture of 20 wt % solutions of V131A (SRC recycle solvent with boiling range of 450°-850° C.); and LSRC (asphaltene-rich SRC) in THF; the second was a 50/50 vol % mixture of 20 wt % solutions of LSRC and THF solubles of KMAC (process stream mixture composed of preasphaltenes, mineral matter and unconverted coal) in THF. The mixed samples were analyzed, and the results were compared to the arithmetic mean of the individually analyzed samples.

Results

Reproducibility. ASE analysis averages ($\bar{x}$) for the weight percent results and standard deviations (s) of the six SRC-I process streams are shown in Table 1. The analysis results for samples V110 (total SRC product liquid, composed of distillate, asphaltenes, preasphaltenes and residue), T102B (distillate tower bottoms), and KMAC were normalized to include the THF-insoluble residue. Standard deviations, which indicate the expected reproducibility of the procedure, were calculated from the results of six replicate assays. The largest standard deviation was determined to be ±1.6 wt%.

Material Balance. LSRC and V131A, as well as THF solubles from the KMAC sample, were combined into 50/50 vol % mixtures. The analysis results for the mixed samples are shown in Table 2, along with the theoretical results based on the arithmetic mean for each 50/50 mixture. The agreement between the analytical and the calculated results is quite good. This study therefore shows that a material balance within 2 wt% can be obtained with analysis of SRC-I process streams of varying compositions in accordance with the invention.

Recovery. The analysis of Wilsonville process streams by the procedure of the invention yields from 90 to 117 mg of the sum of the three fractions. Theoretically, recovery based on the injection of a 0.500-ml sample from a 20% (weight per volume in THF) solution yield 100 mg. The range in yields was traced to variations in the 0.500-ml sample injection loop sizes. These loops were calibrated using a 20.0% solution (weight per volume in THF) of eicosane. The recoveries, given in Tale 3, reflect the 10% variation in loop size. However, the variation in recovery has no effect on the distribution of oils, asphaltenes, and preasphaltenes in an SRC-I sample, as shown in Table 4. The recovery for each fraction by this analysis, performed six times, was found to be within 1 wt%.

TABLE 1

ASE and THF Extraction Weight Percent ($\bar{x}$) and Standard Deviation (s) Results of SRC-I Process Stream Analysis

| Process Stream | | Oils | Asphaltenes | Pre-asphaltenes |
|---|---|---|---|---|
| V110[a] | $\bar{x}$[a] | 63.1 | 16.4 | 20.5 |
| | s | 0.5 | 0.3 | 0.3 |
| T102B[a] | $\bar{x}$[a] | 31.8 | 29.2 | 39.0 |
| | s | 1.2 | 0.5 | 1.5 |
| SRC | $\bar{x}$ | 33.6 | 31.2 | 35.3 |
| | s | 1.2 | 1.0 | 1.1 |
| V131A | $\bar{x}$ | 99.2 | 0.8 | 0.1 |
| | s | 0.9 | 0.9 | 0.2 |
| LSRC | $\bar{x}$ | 66.4 | 28.3 | 5.3 |
| | s | 1.6 | 1.5 | 1.0 |
| KMAC[a] | $\bar{x}$[a] | 17.1 | 21.9 | 61.0 |
| | s | 0.1 | 0.3 | 0.4 |

[a]Excluding THF insolubles.

TABLE 2

ASE Analysis Results for Mixtures of SRC-I Samples

| Mixture | Wt % | | |
|---|---|---|---|
| | Oils | Asphaltenes | Preasphaltenes |
| LSRC/V131A | | | |
| Analyzed | 84.4 | 12.7 | 2.9 |
| Calculated | 82.8 | 14.6 | 2.7 |
| LSRC/KMAC | | | |
| Analyzed | 42.3 | 25.6 | 32.0 |
| Calculated | 41.8 | 25.1 | 33.2 |

TABLE 3

ASE Sample Loop Calibration

| | Loop A | Loop B | Loop C |
|---|---|---|---|
| Mg recovered | 100.1 | 111.3 | 100.8 |
| s[a] | 1.1 | 1.8 | 1.6 |
| Loop size (μl) | 513.3 | 594.5 | 504.0 |

[a]Standard deviation (mg).

TABLE 4

Reproducibility of Weight Percent and Recovery by ASE Analysis of the THF-Soluble V110 Sample

| Run no. | 1 | 2 | 3 | 4 | 5 | 6 | $\bar{x}$ | s[b] |
|---|---|---|---|---|---|---|---|---|
| % oils | 63.3 | 63.5 | 62.7 | 63.5 | 63.6 | 63.8 | 63.1 | 0.6 |
| % asphaltenes | 16.3 | 16.4 | 16.4 | 16.8 | 16.7 | 16.0 | 16.4 | 0.3 |
| % preasphaltenes | 20.2 | 20.1 | 20.9 | 20.7 | 20.7 | 20.2 | 20.5 | 0.3 |
| Mg recovered | 111 | 104 | 113 | 117 | 115 | 117 | 112.8 | 4.9 |

[a]Using sample loop B.
[b]Standard deviation (wt %).

What is claimed is:

1. A continuous elution process for analysis and separation of a sample derived from a coal liquefaction process containing respective fractions comprised of distillate oils, asphaltenes and preasphaltenes by sequential solvent elution through a fluidized bed or inert low surface area solids to acquire the same quantity of said fractions of distillate oils, asphaltenes and preasphaltenes as are initially present in said sample without transfer by co-solubility of any one of said fractions of said sample to another of said fractions which are eluted from said sample, which process comprises:

(a) passing a flow of a first stream of a weakest solvent of eluting solvents upwardly through a bed of low surface area, inert material in a vertically extending column to fluidize said low surface area, inert material and maintaining said fluidization of said low surface area, inert material;

(b) injecting a measured predetermined quantity of said sample into said weakest solvent stream;

(c) continuing said flow of said weakest solvent stream for a first period of time;

(d) collecting a first effluent from said vertically extending column during said flow of said weakest solvent in a first collection container, said first effluent resulting from said flow of said sample and said weakest solvent stream and containing said weakest solvent and said distillate oils fraction of said sample;

(e) terminating said flow of said weakest solvent at the end of said first time period;

(f) passing a flow of a next-to-weakest solvent through said vertically extending column for a second period of time;

(g) collecting a second effluent from said vertically extending column during said flow of said next-to-weakest solvent in a second collection container, said second effluent resulting from said flow of said sample and said next-to-weakest solvent and containing said next-to-weakest solvent and said asphaltenes fraction of said sample;

(h) terminating said flow of said next-to-weakest solvent at the end of said second period of time;

(i) passing a flow of a strongest solvent through said vertically extending column for a third period of time; and (j) collecting a third effluent from said vertically extending column during said flow of said strongest solvent in a third collection container, said third effluent resulting from said flow of said sample and said strongest solvent stream and containing said strongest solvent and said preasphaltenes fraction of said sample, said bed of inert material being fluidized during contact of said solvents with said sample during said elution process to an extent such that co-solubilization of said fractions is eliminated during the elution process.

2. The process according to claim 1 wherein said weakest solvent is of a strength sufficient to dissolve the distillate oils but not the asphaltenes and preasphaltenes, and wherein said period and volume of upward flow during said first time period of step (c) is sufficient to provide that substantially all the distillate oils are dissolved in said weakest solvent stream, whereby said asphaltenes and preasphaltenes are precipitated therein and are thereby deposited on said low surface area, inert material.

3. The process according to claim 2 wherein said next-to-weakest solvent is of a strength sufficient to provide that the asphaltenes on said low surface area, inert material are soluble therein but the preasphaltenes are insoluble therein.

4. The process according to claim 1 wherein said weakest solvent is of a strength sufficient to dissolve the distillate oils but not the asphaltenes and preasphaltenes, and wherein said period and volume of upward flow during said first time period of step (c) is sufficient to provide that substantially all the distillate oils are dissolved in said weakest solvent stream and the asphaltenes and preasphaltenes are precipitated therein and are deposited on said low surface area, inert material, said next-to-weakest solvent is of a strength sufficient to dissolve the asphaltenes on said low surface area, inert material but not the preasphaltenes, and where said strongest solvent is of a strength sufficient to dissolve the preasphaltenes on said low surface area, inert material.

5. The process according to claim 4 wherein said weakest solvent is heptane, said next-to-weakest solvent is benzene, and said strongest solvent is pyridine.

6. The process according to claim 4 wherein said low surface area, inert material comprises beads which are made of glass and which are 90–120 mesh size.

7. The process according to claim 1 wherein after a period of upward flow of said weakest solvent through said column during said first time period of step (c), said column is turned so that subsequent flow of said weakest solvent stream passes downwardly through said column.

8. The process according to claim 7 wherein said column is returned to the initial vertical condition before the end of said second period to provide subsequent flow of said next-to-weakest solvent through said column in an upward direction.

9. The process according to claim 8 wherein said weakest solvent is of a strength sufficient to dissolve the distillate oils but not the asphaltenes and preasphaltenes, and wherein said interval and volume of upward flow during said first time period of step (c) is sufficient to provide that substantially all the distillate oils are dissolved in said weakest solvent stream and the asphaltenes and preasphaltenes are precipitated therein and are deposited on said low surface area, inert material.

10. The process according to claim 1 wherein after a period of upward flow of said weakest solvent through said column during said first time period of step (c), said column is turned so that subsequent flow of said weakest solvent stream passes downwardly through said column, said column is then returned to the initial vertical condition period before the end of said second time period to provide flow of said strongest solvent through said column during said third time period in an upward direction, and after a period of upward flow during said third time period, said column is again turned so that a subsequent solvent stream is passed through said column in a downward direction.

11. The process according to claim 10 wherein said weakest solvent is heptane which dissolves said distillate oils and wherein the asphaltenes and preasphaltenes are insoluble in said heptane, wherein said interval and volume of upward flow during said first time period of step (c) is sufficient to provide that substantially all the distillate oils are dissolved in said weakest solvent stream and the asphaltenes and preasphaltenes are precipitated and deposited on said low surface area, inert material in said column.

12. The process according to claim 11 wherein said next-to-weakest solvent is benzene and said strongest solvent is pyridine.

* * * * *